United States Patent [19]
Nakatani et al.

[11] 4,359,709
[45] Nov. 16, 1982

[54] COMBUSTIBLE GAS SENSOR

[75] Inventors: Yoshihiko Nakatani, Osaka; Masayuki Sakai, Katano; Seiichi Nakatani, Neyagawa; Michio Matsuoka, Ibaraki, all of Japan

[73] Assignee: Matsushita Electric Industrial Co., Ltd., Japan

[21] Appl. No.: 165,008

[22] Filed: Jul. 1, 1980

[30] Foreign Application Priority Data

Jul. 6, 1979 [JP] Japan .................................. 54-86173
Jul. 6, 1979 [JP] Japan .................................. 54-86174

[51] Int. Cl.³ .......................................... H01L 47/00
[52] U.S. Cl. ........................................ 338/34; 422/94
[58] Field of Search ................. 338/34, 13; 73/27 R; 422/94; 204/195 S; 252/519; 23/232 E

[56] References Cited

U.S. PATENT DOCUMENTS

| | | | |
|---|---|---|---|
| 3,251,654 | 5/1966 | Palmer | 23/232 E X |
| 3,695,848 | 10/1972 | Taguchi | 73/27 R X |
| 3,886,785 | 6/1975 | Stadler et al. | 73/27 R X |
| 3,952,567 | 4/1976 | Shinagawa et al. | 338/34 X |
| 3,955,929 | 5/1976 | Kawakami et al. | 73/27 R X |
| 3,999,947 | 12/1976 | Mihara et al. | 338/34 X |
| 4,001,757 | 1/1977 | Sato et al. | 338/34 |
| 4,017,792 | 4/1977 | Heiland et al. | 73/27 R X |
| 4,097,353 | 6/1978 | Kishida et al. | 204/195 S |
| 4,194,994 | 3/1980 | Baresel et al. | 23/232 E X |

FOREIGN PATENT DOCUMENTS 51-108892  9/1976  Japan ..................................... 338/34

Primary Examiner—C. L. Albritton
Attorney, Agent, or Firm—Wenderoth, Lind & Ponack

[57] ABSTRACT

A combustible gas detecting element, the sensitive element of which has at least one material selected from the group consisting of gamma-type ferric oxide ($\gamma$-$Fe_2O_3$) and alpha-type ferric oxide ($\alpha$-$Fe_2O_3$) and has a microstructure with an average grain size smaller than 0.5 micrometers and a porosity of from 35 to 85%. The sensitivity is increased by adding at least one material selected from a group consisting of tin (Sn) and zinc (Zn) in a ratio from 0.5 to 70 mol %, based on stannic oxide (SnO) and zinc oxide (ZnO) relative to the ferric oxide component. The element is manufactured from fine particles obtained by coprecipitating metallic ions from a solution containing Fe ions and at least one member selected from the group consisting of Sn ions and Zn ions, and the fine particles are pressed and then sintered or are formed into a paste, printed on a substrate and then sintered.

5 Claims, 5 Drawing Figures

COMBUSTIBLE GAS SENSOR

This invention relates to a combustible gas detecting element for detecting a combustible gas by being changed in its resistivity upon being subjected to a combustible gas, namely a reducing gas, and provides such an element having a large sensitivity to methane ($CH_4$).

As a rule, the methods for detecting a combustible gas by solid materials include two methods, one of which involves detecting a combustible gas by the temperature rise owing to its combustion on the catalyzer by means of a resistor such as platinum wire, of which electric resistance is dependent upon the temperature. The other of which involves detecting a combustible gas by determining the change in the electrical resistance of a semiconductor accompanied by the adsorption of gas thereon. The former gives an output in proportion to the concentration of gas and accordingly may be used principally for a gas concentration meter and the like. The latter can provide an inexpensive detecting means and accordingly may be used as a gas leak detector and the like.

The present invention provides a gas detecting element of semiconductor type for a combustable gas detecting means according to the latter method.

A gas responsive element is held in an atmosphere of high temperature because a gas detecting element of the semiconductor type requires, in general, a high-speed response. Thus the oxides which are stable in an oxidizing atmosphere are selected as gas responsive elements.

Recently considerable research and development on the materials for a combustible gas detecting element has been conducted, centered on metal oxide semiconductors. This is caused by the big social problem in that the explosions due to combustible gas and the poisoning due to a noxious gas are frequently generated in the home and in a variety of factories.

Liquefied natural gas (LNG) containing methane gas as its principal component has come into wide use in homes in many countries. Thus, a gas detecting element for selectively detecting methane gas, which is the principal component of LNG, is also in remarkably great demand.

Of course, a gas detecting element for responding to methane gas has already been developed. However, such gas detecting elements have a variety of defects such as catalyst poisoning due to a variety of gases, low selectivity for methane gas, great dependence upon the ambient humidity and the like because they contain noble metal catalysts as the activators for the responsive material. Thus, they have no practical use as yet.

It is an object of the present invention to provide a gas detecting element which has suitable characteristics for avoiding the above-described defects and yet which has sufficient sensitivity to methane gas. It is required that a detecting element having great sensitivity to methane gas be remarkably active, because methane gas itself is remarkably stable. Thus, the addition of noble metal catalysts to responsive materials, and the operation of responsive materials at the considerably high temperature and the like have been employed to realize a great sensitivity to methane gas. The gas detecting element according to the present invention can have a large sensitivity to methane even at a very low operating temperature without adding noble metal catalysts.

It was recently found that gamma-type ferric oxide ($\gamma$-$Fe_2O_3$) having a spinel-type crystalline structure has excellent gas detection characteristics. There are various crystalline structures of ferric oxides which are very different from each other in their chemical and physical properties. Among them, best known one is alpha-type ferric oxide ($\alpha$-$Fe_2O_3$) having a corundum-type crystalline structure. Besides, $\gamma$-$Fe_2O_3$, $\beta$-$Fe_2O_3$, $\delta$-$Fe_2O_3$, etc. are known. Among them, only the $\gamma$-$Fe_2O_3$ has actually useful gas detection characteristics.

Although $\gamma$-$Fe_2O_3$ has a large sensitivity to hydrogen, ethane, propane and iso-butane, its sensitivity to methane is not always sufficient.

Also $\alpha$-$Fe_2O_3$ has a remarkably small sensitivity not only to methane but also to ethane, propane and iso-butane, if the sensitive materials are manufactured from the commercial materials. That is to say the conventional ferric oxides do not have a sufficiently large sensitivity to methane, which is the principal component of liquefied natural gas (LNG) used as the main fuel at present.

It is another object of the present invention to provide a sufficiently large sensitivity to methane. $\gamma$-$Fe_2O_3$ has been hitherto considered to be chemically stable to methane with only a small sensitivity to methane while it has a sufficiently large sensitivity to other combustible gases. On the other hand, $\alpha$-$Fe_2O_3$ has been hitherto considered to have a remarkably small sensitivity to combustible gases generally.

The foregoing objectives are surprisingly realized by the provision of a responsive material produced from very fine particles of $\alpha$- or $\gamma$-$Fe_2O_3$, having a large specific surface area.

While the conventional gas detecting element of the metal oxide semiconductor type is generally composed of metal oxides, as the principal component of responsive materials, in which noble metal catalysts are added in order to enhance its sensitivity and improve its response and recovery characteristics, the gas detecting element according to the present invention has a large sensitivity to methane without using noble metal catalysts, and this is realized by controlling the microstructure of responsive element. Thus, the dependency of the conventional combustible gas detecting element upon an ambient humidity, that is the phenomenon in which gas response characteristics of a gas detecting element is dependent upon an ambient humidity, can be remarkably improved.

Also, another feature of the present invention is that the gas detecting element according to the present invention has a small sensitivity to alcohol, conversely, which may be a cause of a false alarm in practical use.

It is necessary to "activate" gas responsive materials by some sort of means in order to impart to them a large sensitivity to methane which is very stable chemically even in the range of low gas concentration. The methods by which gas responsive materials can be "activated" consist principally of the following three ways:
(1) The operating temperature of a gas detecting element is raised.
(2) The activity is chemically enhanced by adding noble metal catalysts.
(3) Responsive materials are composed of metallic oxides having a remarkably small grain size to increase their specific surface area by controlling their microstructure.

It is feared that the life span of a detecting element is shortened in case of (1) in which the operating temperature of a gas detecting element is raised and accordingly this method (1) is not preferable because a gas detecting element must be operated generally in a constant temperature range. Also, $\gamma$-$Fe_2O_3$ is transformed to $\alpha$-$Fe_2O_3$ having a different crystal structure from that of $\gamma$-$Fe_2O_3$ at the temperature over its transition temperature (as a rule, 400° to 600° C. depending upon the method of manufacturing and the composition) and consequently it should be avoided to operate it at an excessively high temperature. The method (2) in which noble metal catalysts are added has been conventionally used for manufacturing the combustible gas detecting element of metal oxide semiconductor type because of its comparative simplicity. Although this method (2) is effective in the enhancement of sensitivity and the improvement of response and recovery characteristics, on the other hand it has the defects such as the random response to a variety of gases, the great dependency upon an ambient humidity or the degradation by poisoning gases. On the contrary to the method (1) and (2), the method (3) can "activate" responsive materials themselves to give a large sensitivity to methane which is chemically stable without changing the operating temperature and the composition.

This invention will be more detailedly described hereinafter with the aid of drawings, in which.

EXAMPLE 1

Figure 1:
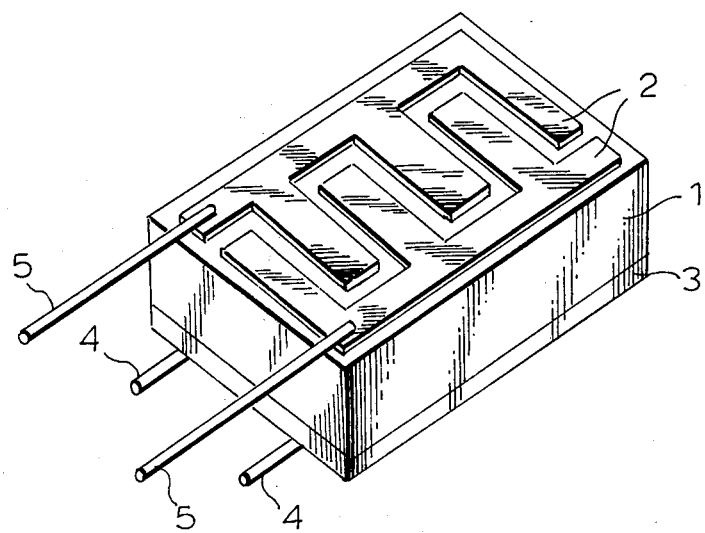
FIG. 1 is a perspective view of an example of a gas detecting element of this invention in the form of a sintered body.
Figure 2:
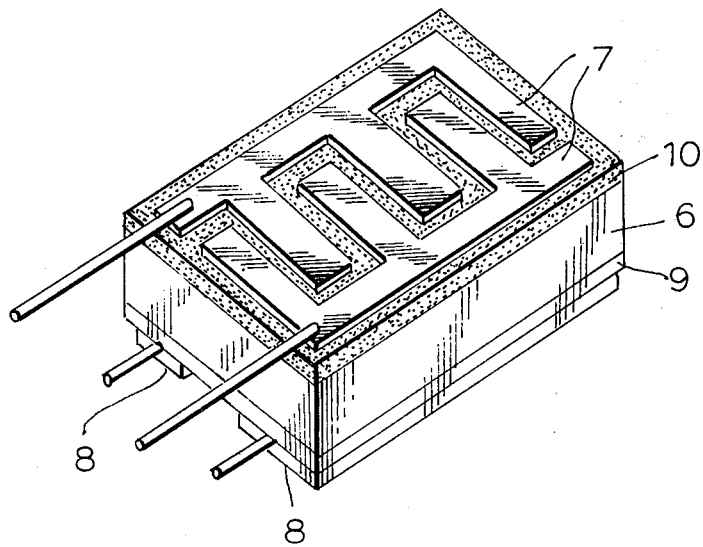
FIG. 2 is a perspective view of an example of a gas detecting element of this invention in the form of a sintered film.

Commercially available ferrous sulfate ($FeSO_4.7H_2O$) 100 g. is dissolved in pure water 2 liters at 50° C. and is stirred. 8 N ammonium hydroxide ($NH_4OH$) is added to the above prepared solution dropwise at a rate of 60 cc/min. until the pH 7. After the addition of ammonium hydroxide, the solution is kept at 50° C. for ten minutes and then is cooled to room temperature. At this stage brownish black coprecipitate is formed. The coprecipitate is filtered by suction and dried at 110° C. for 12 hours.

The dried powders are divided into two portions, one of which is treated with a nitrogen stream containing 20% hydrogen at 400° C. for 1 hour (referred to as V-group hereinafter). The other portion is treated with air at 400° C. for 1 hour (referred to as A-group hereinafter). Thus, the former is transformed to tri-iron tetroxide in the form of powder and the latter is transformed to gamma-type ferric oxide ($\gamma$-$Fe_2O_3$) partially containing alpha-type ferric oxide ($\alpha$-$Fe_2O_3$) in the form of powder. These powders are crushed for 2 hours and then are granulated with an organic binder to obtain particles of 100 to 200 micrometers size. These particles are pressed under a pressure of 400 Kg/cm² to form a rectangular parallelopiped of $2 \times 1.5 \times 3$ mm size. The samples belonging to V-group are sintered in vacuum at 750° C. for 1 hour and then treated in air at 400° C. for 20 hours. Also the samples belonging to A-group are sintered in air at 750° C. for 1 hour. At this stage, the samples belonging to V-group are transformed into a responsive element 1 of $\gamma$-$Fe_2O_3$ and the materials belonging to A-group are transformed into a responsive element 1 of $\alpha$-$Fe_2O_3$. Then a detecting element is fabricated by evaporation of a coating of Au on the surface of such a sintered body to form a pair of semicircular electrodes 2 and a platinum heater 3 is adhered on the reverse side by inorganic adhesives. The gas response characteristics of the detecting elements were investigated by determining an electric resistance between a pair of said Au electrodes by means of a wire-electrode 5, with an operating temperature of 400° C. maintained by controlling an electric current sent to said heaters through a wire-electrode 4.

The microstructure of responsive materials was investigated with a sintered body in the stage preceding the process in which Au electrodes are formed. As a result, it was found that an average grain size of sintered $\gamma$-$Fe_2O_3$ particles and sintered $\alpha$-$Fe_2O_3$ particles was 0.20 micrometers equally and the porosity of sintered $\gamma$-$Fe_2O_3$ and $\alpha$-$Fe_2O_3$ was 68% and 63%, respectively.

The electrical resistance ($R_a$) in air was determined in a measurement vessel having the volume of 50 liters in which dry air was stirred slowly, so as not to generate turbulence therein and the electric resistance ($R_g$) in gas was determined in said measurement vessel through which the gas to be tested, having a purity of 99% or more, was passed at a volume ratio of 10 ppm/sec at the moment when the concentration of gas reached the definite value.

The $R_a$ of the samples belonging to V-group, that is $\gamma$-$F_2O_3$, was 780 k$\Omega$ and $R_a$ of the samples belonging to A-group, that is $\alpha$-$Fe_2O_3$, was 665 k$\Omega$.

Methane ($CH_4$), ethane ($C_2H_6$), propane ($C_3H_8$), isobutane (i-$C_4H_{10}$), hydrogen ($H_2$) and ethyl alcohol ($C_2H_5OH$) were used as gas as to be tested, in the concentration of 0.05%, 0.2% and 1.0%. The dependency of $R_g$ upon the concentration of each gas is shown in Table 1. As shown in this table, all elements have a remarkably small sensitivity to ethyl alcohol while they have a practically sufficient sensitivity to methane, ethane, propane, isobutane and hydrogen. Although $\alpha$-$Fe_2O_3$ has a remarkably low gas response characteristic originally, $\alpha$-$Fe_2O_3$ in which microstructure is controlled in this way has a practically sufficient sensitivity to methane, for which microdetection had been deemed to be difficult.

Although it is well known that also $\gamma$-$Fe_2O_3$ itself has a large sensitivity to propane, isobutane, hydrogen and the like, the microdetection of methane by means of $\gamma$-$Fe_2O_3$ which shows a particularly high chemical stability has been deemed to be difficult. However, $\gamma$-$Fe_2O_3$ having a microstructure controlled according to the present invention has a considerable sensitivity to methane.

Still another feature of a gas detecting element according to the present invention is its small dependency upon an ambient humidity. For example, $R_g$ of the gas detecting element according to the present invention was determined for each gas, at a concentration of 0.2% in an ambient atmosphere of 40° C. in the range of relative humidity from 35 to 95%. Also, the result of this measurement is shown Table 1. In Table 1, $\beta_H$ represents the ratio $R_g(0.2)$ at a relative humidity of 35% to $R_g(0.2)$ at a relative humidity of 95%, that is $R_g(0.2)_{35\%RH}/R_g(0.2)_{95\%RH}$, indicating the magnitude of the dependency of $R_g(0.2)$ upon an ambient humidity. As clearly from the table, the dependency of $R_g(0.2)$ upon an ambient humidity is remarkably small, although some difference is found depending upon the type of gas to be tested. It will be easily found that the effect of the present invention is remarkable when taking into consideration that $\beta_H$ of the conventional gas detecting element of semiconductor type in which noble metal catalysts are added is about 1.25 or more.

EXAMPLE 2

In an Example 1, sintering was carried out at 750° C. for 1 hour in vacuum and in air equally. In this example, the sintering temperature was varied at every 100° C. over the range from 550° to 1,150° C. Gas response characteristics and the dependency of the microstructure of responsive materials upon the sintering temperature were investigated for the gas detecting elements fabricated in the same way as shown in Example 1 thereafter. Sintering was continued for 1 hour.

Figure 3:
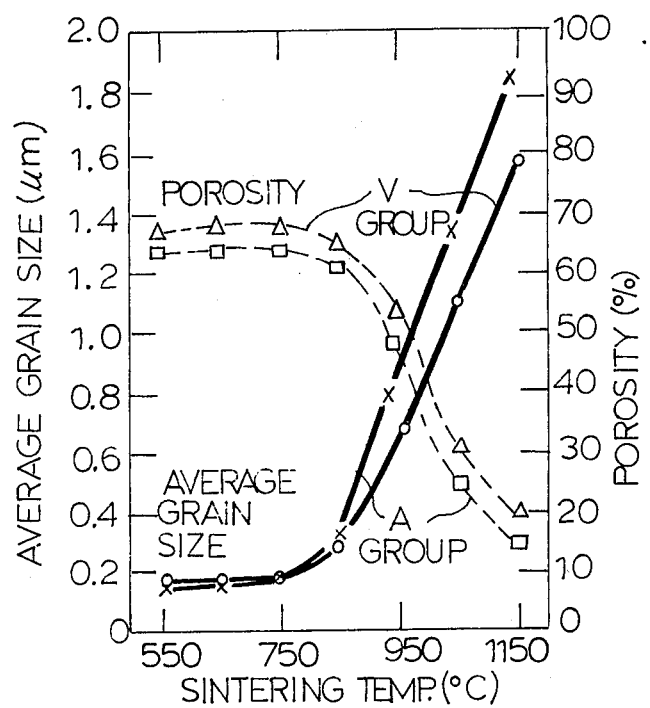
FIG. 3 is a graph showing the dependency of an average grain size and porosity upon a sintering temperature.
Figure 4A:
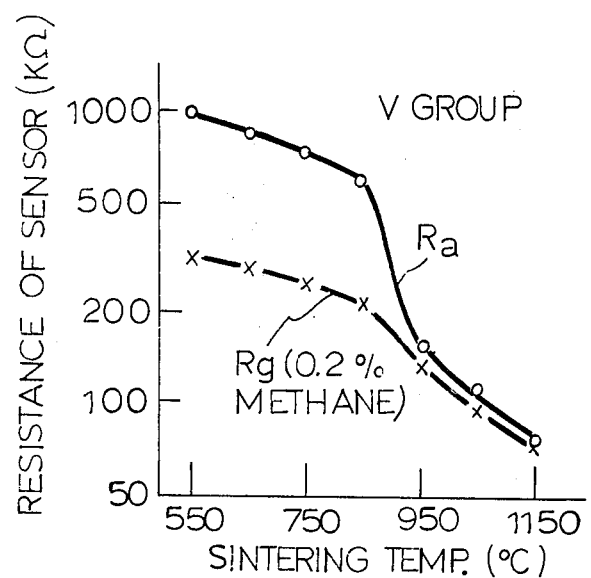
FIGS. 4a and 4b are graphs showing the dependency of electric resistance of a sensor upon a sintering temperature.
Figure 4B:
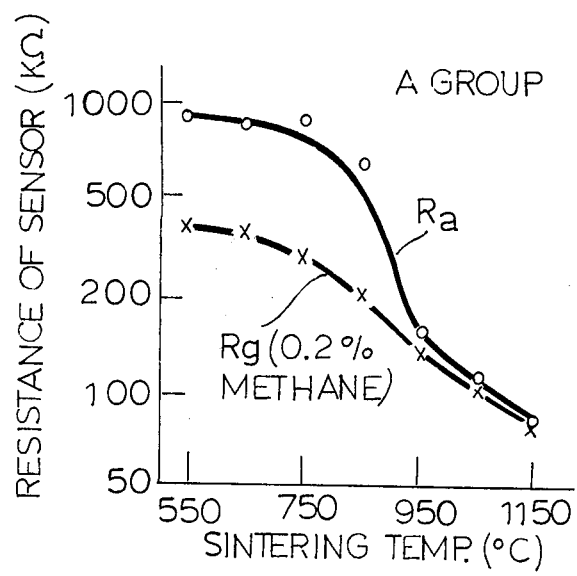

FIG. 3 is a graph showing the relationship between the sintering temperature, an average grain size and porosity. FIG. 4 is a graph showing the relationship between the sintering temperature and gas response characteristics ($R_a$ and and $R_g$ (0.2% methane)). It is clear from the graphs that the growth of grains is promoted and also the porosity is reduced at a sintering temperature of 950° C. or more. Also gas response characteristics undergo a change in correspondence to the changes in the growth of grains and their porosity. It is worth noticing from these results that gas response characteristics of responsive materials are remarkably dependent upon their microstructure even if their composition is constant. That is to say, an average grain size of 0.5 micrometers or more leads to the decrease of an effective specific surface area as well as the activity and consequently to the decrease of the sensitivity to gas as well. Also the porosity of 35% or less leads to the same as above described. On the contrary, the porosity of 85% or more leads to a small mechanical strength and consequently to an element which has no practical use.

As described above, the gas detecting element of the present invention has a practically sufficient sensitivity to methane which has been hitherto deemed to be chemically stable and consequently difficult to be detected in a large sensitivity, even at a considerably low operating temperature such as 400° C. without using noble metal catalysts. Furthermore, the gas detecting element of the present invention has a small sensitivity to alcohol which may be a cause of a false alarm practically and an advantageous small dependency upon ambient humidity.

The sensitivity can be further enhanced by adding other components. Such advantages will be described in detail in the following examples:

EXAMPLE 3

Commercially available ferrous sulfate (FeSO$_4$.7H$_2$O) 160 g is dissolved in 2 liters of pure water kept at 50° C. and stirred sufficiently. Also commercially available zinc sulfate (ZnSO$_4$.7H$_2$O) 35 g is dissolved in pure water 1 liter and stirred sufficiently. The solution of zinc sulfate is poured into the previously prepared Fe ion-containing solution and is stirred sufficiently again. Then, 8 N ammonium hydroxide (NH$_4$OH) solution is added into the above described solution prepared from a zinc sulfate solution and Fe ion-containing solution is added dropwise at a rate of 60 cc/min until the pH of the solution 7. After adding a solution of ammonium hydroxide the solution is kept at 50° C. for 10 min. and then is cooled to room temperature. In this stage brownish black coprecipitate is formed. This coprecipitate is filtered by suction and dried at 110° C. for 12 hours.

The dried powders are divided into two portions, one of which is subjected to a reducing treatment (V-group) and the other of which is subjected to an oxidizing treatment (A-group) in the same way as described in Example 1. Gas response characteristics and a microstructure were investigated for the gas detecting elements belonging to the above described two groups fabricated in the same way as shown in Example 1 thereafter. The results are shown in Table 2.

It is clear from the comparison of Table 2 with the results in Example 1 that the addition of zinc leads to an increase of a sensitivity to methane, ethane, propane and iso-butane and an increase of "resistance change ratio" (change of resistance per unit gas concentration) while a great change is not found in the microstructure. On the other hand, the addition of zinc does not lead to a great difference in a sensitivity to alcohol as well as a dependence upon ambient humidity.

The construction combined with other components such as zinc leads to the increase of a sensitivity to gas as well as a resistance change ratio alone without deteriorating other characteristics. This effect holds for both V-group and A-group to almost the same extent.

This effect can be found not only in case of adding zinc but also in case of adding tin instead of zinc or adding both zinc and tin.

The effect owing to the combined addition of such components will be shown in The following example 4:

EXAMPLE 4

An iron ion-containing aqueous solution, a tin ion-containing aqueous solution and a zinc ion- containing aqueous solution are prepared in the same way as shown in Example 3 from commercially available ferrous sulfate (FeSO$_4$.7H$_2$O), stannic chloride (SnCl$_4$.5H$_2$O) and zinc sulfate (ZnSO$_4$.7H$_2$O), respectively. Coprecipitates are obtained by adding ammonium hydroxide (NH$_4$OH) to the solution a mixture of different mixture ratios consisting of these three aqueous solutions. Coprecipitates are dried and crushed for use in preparing the responsive materials.

Thus obtained fine particular materials are granulated with an organic binder to obtain the grains of 100 to 200 micrometers size. A variety of such powders are pressed by the pressure of 400 kg/cm$^2$ to form a rectangular parallelopiped (2×1.5×3 mm) and the pressed products are sintered in air at 800° C. for 1 hour. Then a detecting element is fabricated by an evaporative coating of Au on the surface of such a sintered body 1 to form a pair of semicircular electrodes 2 and platinum heater 3 as adhered to the reverse side by inorganic adhesives. The gas response characteristics were determined at an operating temperature of 400° C. held constant by controlling an electric current passing through said heaters 3. The results are shown in Table 3. Methane, ethane, propane, iso-butane, hydrogen and ethyl alcohol were used as gases to be tested as in case of Example 1 and Example 3. $R_g$ is the value at the gas concentration of 0.2%. $\beta_H$ is the value for isobutane which shows the largest $\beta_H$ of all gases to be tested.

It is clear from Table 3 that the addition of tin and zinc in a total ratio under 0.5 mol. %, based on SnO$_2$ and ZnO, does not lead to the realization of the effect expected by their addition. On the contrary, their addition in a total ratio over 70 mol. % leads to an extraordinary decrease of resistance, a scattered resistance and a large time-change in resistance to a gas detecting element which has no practical use while some gas detecting elements have some degree of gas response characteristics. This is the reason why the total amount of Sn and Zn is limited to the range from 0.5 mol. % to 70 mol. %, based on their oxides.

Thus, the gas detecting element according to the present invention makes a high accuracy detection of methane which, is in great demand nowadays, possible without using noble metal catalysts, by controlling the microstructure of sensitive elements, in particular an average grain size and the porosity of the sensitive materials consist and by operating the element at a comparatively lower temperature. Besides, the gas detecting element according to the present invention has a small sensitivity to ethyl alcohol and a remarkably small dependency upon an ambient humidity and consequently makes a combustible gas detection by which a false alarm is seldom given, practically possible.

In the above-described examples, the gas detecting element using a sintered body as gas sensitive materials was described. It is, however, clear that the gas detecting element according to the present invention is not limited to the use of a sintered body but other bodies, such as a thick film may be used. The other components may be added in order to improve the characteristics of a gas detecting element.

The following examples relate to the cases when a sintered film is used as a sensitive materials.

EXAMPLE 5

Commercially available ferrous sulfate ($FeSO_4.7H_2O$) 160 g is dissolved in 2 liters pure water kept at 50° C. and stirred sufficiently. Also, commercially available stannic chloride ($SnCl_4.5H_2O$) 80 g is dissolved in 1 liter pure water and is stirred sufficiently. The stannic chloride aqueous solution is poured into the ferrous sulfate aqueous solution and is stirred sufficiently again. At this stage, the color of the solution is changed to yellow. Then, 8 N ammonium hydroxide ($NH_4OH$) solution is added to the solution mixture consisting of a stannic chloride aqueous solution and a ferrous sulfate aqueous solution is added dropwise with stirring at a rate of 60 cc/min. until the pH of the solution is 7. After the addition of ammonium hydroxide, the solution is kept at 50° C. and then is cooled to a room temperature. At this stage, a brownish black coprecipitate is obtained. This coprecipitate is filtered by suction and is dried at 110° C. for 12 hours. The dried blackish grey fine particles are crushed for 2 hours to use as raw materials for sensitive materials. After these particles were granulated to form into the grains of 50 to 100 micrometers size, they are transformed into a paste by adding polyethylene glycol. On the other hand, a pair of semicircular electrodes 7 is formed by printing gold paste in semicircular shape at 0.5 mm intervals on the surface of an alumina base plate 6 of 5×5×0.5 mm size which is used as the base plate of a gas detecting element and then being subjected to a heat treatment. Commercially available glazed heaters made of ruthenium oxide are printed between gold electrodes 8 on the reverse side of an alumina base plate and are subjected to a heat treatment to form heaters 9. Said paste coated on the surface of said base plate in the thickness of about 70 micrometers is naturally dried at a room temperature and then fired at 650° C. for 1 hour in air. In this process, the volatile component of paste is evaporated to obtain a sintered film 10 having a sufficient mechanical strength for practical use. The thickness of these gas responsive materials is preferably about 40 micrometers.

Then, its gas response characteristics were determined at the temperature of responsive materials (operating temperature) of 400° C. kept by electrifying said heaters.

The resistance ($R_a$) in air was determined in a measurement vessel having the volume of 50 liters in which dry air stirred slowly not so as to generate turbulence therein and the resistance ($R_g$) in gas was determined in said measurement vessel through which gas to be tested having the purity of 99% or more passed at a volume ratio of 10 ppm/sec at the moment when the concentration of gas reached the definite value.

Methane ($CH_4$), ethane ($C_2H_6$), propane ($C_3H_8$), isobutane ($i-C_4H_{10}$), hydrogen ($H_2$) and ethyl alcohol ($C_2H_5OH$) were used as the gas to be tested in the quantity of 0.05%, 0.2% and 1.0%. $R_a$ was 860 k$\Omega$ and the dependency of $R_g$ upon the concentration of each gas was as shown in Table 4.

As clearly shown in this table, a gas detecting element manufactured in this way has a remarkably small sensitivity to ethyl alcohol while it has a particularly large sensitivity to methane, ethane, propane, isobutane, and hydrogen.

Thus, the gas detecting element according to the present invention has a large sensitivity not only to methane, ethane, hydrogen and isobutane, which are the components of liquefied natural gas (LNG) and general city gas (mixed gas) but also to propane and isobutane which are the principal components of LPG even when its sensitive material is a sintered film. Thus, the gas detecting element according to the present invention is characterized by a practical and sufficient sensitivity to methane which is the principal component of natural gas and has been deemed to be difficult to detect sensitively by means of a gas detecting element of the semi-conductor type without containing noble metal catalysts.

Furthermore, as shown in the above described examples, one of the features of the gas detecting element according to the present invention is its small dependency upon an ambient humidity. For example, $R_g(0.2)$ of the gas detecting element according to the present invention was determined for each gas having a concentration of 0.2% in an ambient atmosphere of 40° C. in the range of relative humidity from 35 to 95%. In Table 4, $\beta_H$ represents the ratio $R_g(0.2)$ at a relative humidity of 35% to $R_g(0.2)$ at a relative humidity of 95%, indicating the magnitude (extent) of the dependency of $R_g(0.2)$ upon an ambient humidity. As clearly shown from the table, the dependency of $R_g(0.2)$ upon an ambient humidity is remarkably small, although some difference is found depending upon the sort of gas to be tested. It will be easily found that the effect of the present invention is remarkable by taking into consideration that the $\beta_H$ of the conventional gas detecting element of semiconductor type in which noble metal catalysts are added is about 1.25 or more.

Gas sensitive materials were fabricated from commercially available materials powder and their gas response characteristics were investigated in order to confirm the effect of the present invention. That is to say, the composition consisting of $Fe_2O_3$ 80 mol %, $SnO_2$ 10 mol % and ZnO 10 mol % was obtained from commercially available $Fe_2O_3$, $SnO_2$ and ZnO instead of the powders obtained by the coprecipitating method according to the present invention. This example will be described in detail hereinafter:

EXAMPLE 6

The mixture consisting of commercially available special grade reagent ferric oxide, stannic oxide and zinc oxide in a ratio of $Fe_2O_3:SnO_2:ZnO=80$ mol %:10 mol %:10 mol % 100 g is obtained by blending them for 5 hours by means of a ball mill. Then, the mixture is dried in air of 200° C. for 20 hours. The thus obtained powders are granulated, pressed and a sintered to manufacture a gas detecting element in the same way as Example 4. The gas responsive material obtained in this way had a porosity of 46% and the $R_a$ at the operating temperature of 400° C. was 785 kΩ, which was little different from 696 kΩ in case of the Example 4. However, $R_g(0.2)$ for methane, ethane, propane, isobutane and hydrogen was 656 kΩ, 640 kΩ, 630 kΩ, 621 kΩ and 683 kΩ, respectively. It has a remarkably small sensitivity to to each gas.

It can be thought that the average grain size of $Fe_2O_3$, $SnO_2$ and ZnO used in this example is about 2.5 microns, 8.6 microns and 4.5 microns, respectively and accordingly the specific surface area of a responsive material fabricated is small and as the result its activity is lowered and its gas response characteristics is remarkably lowered.

That is to say, a responsive material shows a remarkably different gas response characteristics depending upon the average grain size of materials powder used despite the same composition. This difference gives a true account of the effect of the present invention.

As described above, the combustible gas detecting element according to the present invention has a large sensitivity to a combustible gas such as methane which has been deemed to be difficult to detect sensitively unless noble metal catalysts are used. Besides, it has a remarkably smaller sensitivity to alcohol which is said to be the principal cause of the false alarm than to said combustible gas. That is to say, it shows a high selectivity. Also it has a small dependency upon water vapor (humidity) which is another cause of a false alarm.

Thus, the gas detecting element according to the present invention can be expected to greatly contribute in a wide variety of fields where a demand for natural gas is being increased, such as in gas detectors, various kinds of gas kitchen units and gas security systems.

Although $FeS_4 \cdot 7H_2O$, $ZnS \cdot 7H_2O$ and $SnCl_4 \cdot 5H_2O$ are used as the materials for preparing aqueous solutions in the examples of the present invention, they need not be limited to those described above. It goes without saying that the materials forming an aqueous solution containing each metallic ion may be used. Also metallic ions other than stannic ions and zinc ions may be added in order to still further improve a gas response characteristics.

TABLE 1

| Kind of gas | $R_g$ (kΩ) 0.005% | 0.2% | 1.0% | $\beta_H$ |
|---|---|---|---|---|
| V group | | | | |
| methane | 490 | 260 | 120 | 0.98 |
| ethane | 435 | 228 | 106 | 1.03 |
| propane | 394 | 203 | 91.8 | 1.04 |
| isobutane | 376 | 188 | 84.5 | 1.04 |
| hydrogen | 361 | 181 | 80.4 | 1.02 |
| ethyl alcohol | 693 | 468 | 302 | 1.03 |
| A group | | | | |
| methane | 451 | 249 | 126 | 0.94 |
| ethane | 406 | 220 | 108 | 0.99 |
| propane | 381 | 204 | 97.6 | 1.02 |
| isobutane | 364 | 194 | 93.2 | 1.04 |
| hydrogen | 338 | 179 | 85.5 | 1.03 |
| ethyl alcohol | 542 | 393 | 254 | 1.02 |

TABLE 2

| Group | Average grain size | porosity | Kind of gas | $R_a$ (kΩ) | $R_g$ (kΩ) 0.05% | 0.2% | 1.0% | $\beta_H$ |
|---|---|---|---|---|---|---|---|---|
| V group | 0.16 μm | 66% | methane | 540 | 188 | 81.3 | 30.4 | 0.95 |
| | | | ethane | | 167 | 73.7 | 28.2 | 1.01 |
| | | | propane | | 161 | 70.5 | 26.6 | 1.01 |
| | | | isobutane | | 150 | 65.4 | 25.1 | 1.04 |
| | | | hydrogen | | 132 | 59.0 | 22.3 | 1.03 |
| | | | ethyl alcohol | | 320 | 208 | 117 | 1.02 |
| A group | 0.17 μm | 64% | methane | 467 | 191 | 82.5 | 33.3 | 0.94 |
| | | | ethane | | 170 | 75.2 | 29.9 | 0.98 |
| | | | propane | | 166 | 73.6 | 30.4 | 1.01 |
| | | | isobutane | | 160 | 68.3 | 27.6 | 1.04 |
| | | | hydrogen | | 141 | 64.2 | 24.6 | 1.03 |
| | | | ethyl alcohol | | 360 | 229 | 130 | 1.02 |

TABLE 3 operating temperature 400° C.

| Mixing ratio (mol. %) SnO$_2$ | ZnO | $R_a$ (kΩ) | $R_g$ (0.2) (kΩ) methane | ethane | propane | isobutane | hydrogen | ethyl alcohol | $\beta_H$ (isobutane 0.2%) | Microstructure average grain size (μm) | porosity (%) |
|---|---|---|---|---|---|---|---|---|---|---|---|
| 0.1 | 0.1 | 648 | 503 | 465 | 443 | 431 | 391 | 635 | 1.02 | 0.20 | 63* |
| 0.5 | 0 | 640 | 406 | 371 | 354 | 338 | 329 | 590 | 1.03 | 0.21 | 66 |
| 5.0 | 5.0 | 663 | 313 | 294 | 290 | 276 | 261 | 488 | 1.04 | 0.19 | 64 |
| 10.0 | 10.0 | 696 | 246 | 213 | 186 | 170 | 159 | 399 | 1.06 | 0.18 | 63 |
| 30.0 | 40.0 | 716 | 278 | 260 | 241 | 220 | 218 | 501 | 1.05 | 0.17 | 70 |
| 70.0 | 0 | 5230 | 1060 | 803 | 768 | 744 | 709 | 3820 | 1.06 | 0.11 | 76 |
| 0 | 70.0 | 260 | 42 | 38 | 36 | 32 | 29 | 176 | 1.06 | 0.15 | 69 |
| 40.0 | 40.0 | 120 | 73 | 70 | 61 | 60 | 53 | 96 | 1.05 | 0.17 | 73* |

TABLE 3-continued

| | | | operating temperature 400° C. | | | | | | Microstructure | |
|---|---|---|---|---|---|---|---|---|---|---|---|
| Mixing ratio (mol. %) | | $R_a$ | $R_g$ (0.2) (kΩ) | | | | | | $\beta_H$ (isobutane | average grain size | porosity |
| $SnO_2$ | ZnO | (kΩ) | methane | ethane | propane | isobutane | hydrogen | ethylalcohol | 0.2%) | (μm) | (%) |
| 0 | 85 | 1260 | 1010 | 860 | 695 | 628 | 896 | 916 | 1.08 | 0.15 | 70* |
| 85 | 0 | | properties largely vary from sample to sample | | | | | | | 0.12 | 72* | samples denoted with * are those for comparison

TABLE 4

| $R_a$ = 860 kΩ operating temperature 400° C. | | | | |
|---|---|---|---|---|
| Kind of gas | $R_g$ (kΩ) | | | $\beta_H$ |
| | 0.05% | 0.2% | 1.0% | |
| methane | 490 | 278 | 146 | 0.97 |
| ethane | 458 | 259 | 133 | 1.02 |
| propane | 446 | 240 | 120 | 1.05 |
| isobutane | 418 | 227 | 114 | 1.06 |
| hydrogen | 390 | 206 | 99 | 1.04 |
| ethyl alcohol | 780 | 540 | 322 | 1.03 |

What is claimed is:

1. A combustible gas detecting element, containing a sensitive element which comprises alpha-type ferric oxide ($\alpha$-$Fe_2O_3$) having a microstructure with an average grain size smaller than 0.5 micrometers and a porosity of from 35 to 85%.

2. The combustible gas detecting element according to claim 1, wherein said sensitive element is a sintered body obtained by pressing fine particles of said iron oxide and then sintering.

3. A combustible gas detecting element, containing a sensitive element which comprises alpha-type ferric oxide ($\alpha$-$Fe_2O_3$) having a microstructure with an average grain size smaller than 0.5 micrometers and a porosity of from 35 to 85% and at least one member selected from the group consisting of stannic and zinc oxides.

4. The combustible gas detecting element according to claim 3, wherein said sensitive element is a sintered body obtained by pressing fine particles of said iron oxide with stannic and zinc oxides and then sintering.

5. The combustible gas detecting element according to claim 3, wherein said sensitive element consists of a sintered film obtained by transforming said iron oxide into a paste, printing the paste on a substrate and then sintering the printed paste.

* * * * *